United States Patent [19]

Kothe et al.

[11] Patent Number: 5,164,487

[45] Date of Patent: Nov. 17, 1992

[54] MANUFACTURING INTRAVENOUS TOLERABLE IMMUNOGLOBULIN-G PREPARATION

[75] Inventors: Norbert Kothe, Kronberg; Dieter Rudnick, Dreieich; Detlef Piechaczek, Munster; Herwald Klein, Weiterstadt; Detlef Rohm; Michael Kloft, both of Darmstadt, all of Fed. Rep. of Germany

[73] Assignee: Biotest Pharma GmbH, Dreieich, Fed. Rep. of Germany

[21] Appl. No.: 669,782

[22] Filed: Mar. 15, 1991

[30] Foreign Application Priority Data

Mar. 22, 1990 [EP] European Pat. Off. ........ 90105405.6

[51] Int. Cl.$^5$ .............................................. C07K 15/14
[52] U.S. Cl. .................. 530/389.1; 530/380; 530/389.4; 530/389.5; 530/390.5
[58] Field of Search ............................ 530/387.1, 380

[56] References Cited

U.S. PATENT DOCUMENTS 3,916,026 10/1975 Stephan ................................. 514/21
4,939,176 7/1990 Serg et al. ........................... 530/380

FOREIGN PATENT DOCUMENTS 0268973 6/1988 European Pat. Off. .
0338229 10/1989 European Pat. Off. .
0346217 12/1989 European Pat. Off. .

OTHER PUBLICATIONS

Journal of Immunological Methods, vol. 65, 1983, Holland, pp. 269-271; Russo, C. et al: "Purification of IgG monoclonal antibody by caprylic acid precipitation".
Chemical Abstracts, vol. 103, No. 13, Sep. 1985, Columbus, Ohio, USA, Goheen, S.C. et al.: "Purification of human serum gamma globulins by hydrophic interaction high-performance liquid chromatography", p. 458; Col. 1, Ref. No. 103013.
Vox Sang. 52: 281-290 (1987), "An Animal Model for the Detection of Hypotensive Side Effects of Immunoglobulin Preparations".
Thrombosis Research 31, 351-364, 1983, "Prekallikrein, HMW-Kininogen and Factor XII in Various Disease States".
Archives of Biochemistry and Biophysics 134, pp. 279-284 (1969), "The Isolation of IgG from Mammalian Sera with the Aid of Caprylic Acid".
Archives of Biochemistry and Biophysics, vol. 89, 1960, pp. 218-220; Chanutin A. et al.: "The precipitation of plasma proteins by short-chain fatty acids".
Preparative Biochemistry, vol. 14, No. 1, 1984, pp. 1-17; Habeeb, A. et al: "Preparation of human immunolglobulin by caprylic acid precipitation".
Develop. biol. Standard, vol. 67, pp. 257-265 (S. Karger, Basel, 1987).
Habeeb and Francis, Prep. Biochem. 14(1) 1-17, 1984. Preparation of Human Immunoglobulin.
Vox Sang. 23165-175, 1972. Pejaudier et al. Preparation of Human IgA as a By-Product of Routine Fractionation.

Primary Examiner—Merrell C. Cashion, Jr.
Assistant Examiner—P. L. Touzeau
Attorney, Agent, or Firm—Sprung Horn Kramer & Woods

[57] ABSTRACT

Method of manufacturing an intravenously tolerable immunoglobulin-G preparation that is free of aggregates, vasoactive substances and proteolytic enzymes and accordingly appropriate for all types of patients, especially immunosuppressed patients, from a starting material that contains immunoglobulin G but from which the coagulation factors have been removed. The starting material is treated with 0.4 to 1.5% by volume of octanoic acid and then chromatographed, especially on an ion or cation exchanger or hydrophobic matrix.

15 Claims, No Drawings

MANUFACTURING INTRAVENOUS TOLERABLE IMMUNOGLOBULIN-G PREPARATION

BACKGROUND OF THE INVENTION

The invention concerns the method of manufacturing an intravenously tolerable immunoglobulin-G preparation.

Immunoglobulin-G preparations obtained from human plasma have been employed for many years to treat inherited and acquired immune-deficiency diseases. The immunoglobulin was initially obtained from human blood plasma by fractional precipitation with ethanol. These preparations, however, could be employed only intramuscularly since intravenous administration was accompanied by extremely serious side effects.

Dosage is limited in intramuscular administration. To obtain a high enough level of immunoglobulins for effective treatment it would accordingly be desirable to be able to make intravenously tolerable immunoglobulin-G preparations.

Various approaches to the problem have already been described. The immunoglobulin-G molecule has been split with enzymes or modified with chemical reagents for example. Other methods of obtaining intravenously tolerable preparations involve precipitation, adsorption and chromatography.

Reviews of the methods currently employed are provided in Krankenhauspharmazie 6, 5 (1985), 226-231 and in Der Bayerische Internist 9, 1 (1989), 36-44.

Although all the preparations described therein can be administered intravenously, they exhibit various drawbacks, depending on how they are prepared. The enzymatically split immunoglobulins for example have a severely curtailed intravascular half life and are incapable of triggering the complement activation requisite for effective defense against infections. Nor do the chemically modified preparations carry out the full range of biological functions due to their short intravascular half life and unsatisfactory complement activation.

To eliminate the aforesaid drawbacks, therefore, improved methods of manufacturing an intravenously tolerable unmodified immunoglobulin-G have been developed.

German A 3 039 855 for example discloses filtering over a polysulfone membrane, especially to remove polymeric substances (aggregates).

German A 3 641 115 proposes purification with polyethylene glycol to remove aggregates.

Neither of these processes, however, allows the elimination of proteolytic activities or vasoactive substances. These substances, which may occur in immunoglobulin-G preparations, include in particular prekallikrein activator, prekallikrein, kininogen and kallikrein. They are notoriously capable of causing serious side effects and especially of triggering hypotensive reactions (cf. M. F. Makula et al., Developm. biol. Standard 67 (1987), 257-65 and W. K. Bleeker et al, Vox Sang. 52 (1987), 281-290).

Attempts to remove proteolytic enzymes by adsorption on bentonite, silica gel, barium sultate, active carbon, or affinity exchangers have not succeeded in eliminating all the deleterious proteases and, depending on the method of manufacturing the immunoglobulin-G preparation, immunological and enzymatic tests have shown it still to contain varying levels of prekallikrein, kininogen and kallikrein even when the presence of any significant level of prekallikrein activator was impossible to identify.

The administration of such preparations, containing the aforesaid substances, to immunosuppressed patients has led to severe side effects even though the substances are highly tolerable intravenously in other applications. Thus, kallikrein can be released in the presence of prekallikrein even when no prekallikrein activator is detected and can release in turn the vasoactive bradykinin from the high molecular-weight kininogen. The result is a drop in blood pressure that is more or less marked in accordance with concentration. This must be taken into consideration in particular with patients with a malfunction in their inhibitor potential, as in the case of immunosuppression.

A generally applicable intravenously tolerable immunoglobulin-G preparation must accordingly be
 a) free of aggregates, with an accordingly strictly low and unspecific complement-system activation,
 b) free of proteolytic enzymes,
 c) free of such vasoactive substances from the clotting and kinin systems as prekallikrein activator, prekallikrein, kininogen, kallikrein, Factor XI and Factor XII, and
 d) biologically intact, meaning that the structure of the Fc component of the immunoglobulin G is unaltered by the manufacturing process and that no chemical modification is employed.

The object of the present invention is to manufacture an intravenously tolerable immunoglobulin-G preparation that can be employed in all types of patients and is free of aggregates, vasoactive substances, and proteolytic activity from a starting material that contains an immunoglobulin. Examples of such a starting material are plasma with the coagulation factors removed or a serum fraction (Cohn's paste II or II-III) that contains immunoglobulin-G for example.

This object is attained in accordance with the invention by treating the starting material with 0.4-1.5% by volume of octanoic acid and subjecting it to chromatography.

The uses of octanoic acid are described in the literature (Biochemistry and Biophysics 134[1969], 279-84). Concentrations of approximately 6.8% by volume are employed to precipitate proteins from plasma or serum, leaving immunoglobulin-G in the supernatant.

It has surprisingly now been discovered that concentrations of 0.4 to 1.5% by volume and preferably of 0.8 to 1.0% by volume of octanoic acid can be employed to eliminate specifically proteolytic enzymes and such compounds as prekallikrein, kallikrein and kininogen that trigger vasoactive reactions, from previously purified immunoglobulin-G solutions with no significant precipitation of protein.

The octanoic acid can then be centrifuged out of such a purified immunoglobulin-G solution or preferably filtered out while having calcium ions added to it.

The effectiveness of the octanoic acid treatment in removing proteolytic enzymes and vasoactive substances from immunoglobulin-G solutions (with a raw immunoglobulin-G fraction obtained from a Cohn procedure as described in Example 1 as a starting material) will be evident from Tables 1 and 2, wherein
 + +means strongly positive,
 I means positive, and
 —means negative.

TABLE 1

| Octanoic acid (% by volume) | Proteolytic activity (units per liter) |
| --- | --- |
| 0.0 | 850 |
| 0.4 | 23 |
| 0.6 | 1 |
| 0.8 | 0 |
| 1.0 | 0 |

TABLE 2

| Octanoic acid (% by vol) | Prekallikrein* | Kallikrein* |
| --- | --- | --- |
| 0.0 | ++ | ++ |
| 0.8 | − | − |
| 1.0 | − | − |
| 1.5 | − | − |

*Determined by Ouchterlony's immunodiffusion. Starting from a raw immunoglobulin-G fraction obtained by chromatography as described in Example 5.

As these results demonstrate, vasoactive substances and proteolytic enzymes can be removed from solutions that contain immunoglobulin-G.

Aggregated immunoglobulin-G molecules can be chromatographed out of the solution in a subsequent step.

Chromatography phases based on silica gel or a polymer are appropriate, and either cationic or anionic exchangers can be employed.

Preferred are chromatography phases that are appropriate for high-performance liquid chromatography (HPLC), a method that can be employed to economically and rapidly manufacture large volumes of immunoglobulin-G.

When such cation exchangers as CM-Accell(®), SP-Spherodex(®), SP-Trisacryl-LS(®) or Fraktogel-TSK-SP650(®) are employed, the salt concentration of the eluents is adjusted to 50-200 moles of sodium chloride and the pH to 4.0-6.0. In these conditions the aggregates will attach to the phase and the purified immunoglobulin-G will pass through the matrix without adhering to it.

The same method an also be employed with such anion exchangers as QMA-Accell(®) and DEAE-Spherosil(®) to remove aggregates from immunoglobulin-G solutions if the ion concentrationis adjusted to 0 to 50 mmoles of sodium chloride and the pH to 6.0 to 8.0.

It has also been demonstrated that the aforesaid chromatography phases can be employed to remove vasoactive substances, especially when cation exchangers or hydrophobic phases are employed Preferred for this purpose are chromatography phases based, as are CM-Accell(®), SP-Spherodex-M(®), and Polypropyl A(®), on silica gel or phase based, as are SP-Trisacryl-LS (®), on synthetic polymers.

If a cation exchanger is employed, the ionic strength and pH of the eluent must allow the purified immunoglobulin-G fraction to travel through the column unimpeded while retaining the contaminants in the chromatography phase.

If CM-Accell(®) is employed, the buffer will for example have a concentration of 50-200 mmoles of sodium chloride and a pH of 4.0-6.0.

If the immunoglobulin is purified by hydrophobic interaction chromatography on Polypropyl A(®), the immunoglobulin-G solution will be attached to the phase with a high molar ammonium sulfate buffer, the contaminants will be rinsed out, and the immunoglobulin-G fraction will be eluted with a linearly decreasing ionic-strength gradient.

Table 3 illustrates the effectiveness of chromatography for removing vasoactive substances from solutions that contain immunoglobulin G.

TABLE 3

| IgG Fraction | Prekallikrein* | Kallikrein* |
| --- | --- | --- |
| Untreated** | ++ | ++ |
| SP chromatography | − | − |
| CM chromatography | − | − |
| Polypropyl A ® chromatography | neg | neg |

*Determined by Ouchterlony's immunodiffusion
**Starting with a raw immunoglobulin-G fraction obtained by chromatography as described in Example 5.

High-purity intravenously tolerable immunoglobulin-G preparations can accordingly be manufactured by treating them in accordance with the invention with octanoic acid and/or chromatography. The starting material can be a gamma-globulin fraction (Cohn's paste II or II-III or the corresponding solutions) obtained by conventional Cohn's fractionation as occurs in large quantities in the industrial manufacture of human albumin. The method in accordance with the invention can also be applied to chromatographically isolated immunoglobulin-G fractions and to those obtained by precipitation with ammonium sulfate or polyethylene glycol. These starting materials can be obtained from normal-donor pools and preferably from donors specially selected for high antibody titers against viral, bacterial or cellular antigens.

The starting material for the method in accordance with the invention is a raw fraction containing immunoglobulin G that is obtained by chromatography or by Cohn processes and is sterilized. Chromatography fractions usually contain approximately 0.5 to 1.5% of aggregates, which are preferably completely removed on such cation exchangers as CM-Accell(®) If the procedure starts with a Cohn's paste II or II-III that contains up to 5% of aggregates, they can be removed in accordance with the invention with CM-Accell(®) or QMA-Accell(®). Vasoactive substances can also be removed by chromatography as previously described herein.

If proteolytic enzymes are present, they can be removed initially with octanoic acid, although this is unnecessary for immunoglobulin-G solutions distinguished by high purity.

Since the plasma or serum fractions employed in the method in accordance with the invention are potentially contaminated with such human-pathogenic viruses as hepatitis A, B, non-A, non-B and human-immunodeficiency viruses, it is preferable to sterilize the immunoglobulin-G solutions. This can be done, preferably prior to chromatography, with β-propiolactone, TNBP+Tween, TNBP+sodium cholate, or TNBP, optionally in combination with ultraviolet radiation. Especially preferred is sterilization with 0.03-0.1% of β-propiolactone along with ultraviolet light.

The products manufactured in this way in accordance with the invention can be stored liquid or lyophilized.

The advantage of the method in accordance with the invention is that an extremely wide range of starting materials that contain immunoglobulin G can be simply and rapidly purified to the extent that the resulting pure products can be intravenously administered without side effects to all types of patients and especially to immunosuppressed patients.

Animal tests of the tolerability of the preparations manufactured in accordance with the invention in comparison with that of products manufactured according to the state of the art will now be described.

One model is the rat (cf. Bleeker et al., Vox Sang. 52[1987], 281-290), and the effects on its blood pressure and heart rate of vasoactive substances of the type that may be present in conventional products were studied. Table 4 summarizes the results.

TABLE 4

| Preparation | | % Deviation in b.p. | Heart rate | Vasoactive substance | | |
|---|---|---|---|---|---|---|
| | | | | Prekallikrein[1] | Kallikrein[1] | Kininogen[1] |
| 1[2] | (ref.) | −30 | +6 | + | + | + |
| 2[2] | (ref.) | −42 | −8 | ++ | + | + |
| 3[2] | (ref.) | −32 | +2 | ++ | + | + |
| 4* | (inv.) | −2 | −4 | − | − | − |
| 5* | (inv.) | −3 | +3 | − | − | − |
| 6** | (inv.) | −4 | +1 | − | − | − |
| 7** | (inv.) | 0 | +1 | − | − | − |
| El. from 7*** | | −13 | +10 | ++ | + | + |

[1] Determined by Ouchterlony's immunodiffusion
[2] Raw immunoglobulin-G fraction obtained by chromatography as described in Example 5.
*Manufactured as described in Example 8.
**Manufactured as described in Example 9.
***Column eluate from preparation 7 employed as a positive control (containing vasoactive substances).

The solution is considered tolerable at bloodpressure drops to −10%.

As the results of this test indicate, preparations purified over an ion exchanger in accordance with the invention occasion almost no deviations in blood pressure or heart rate, which documents their high tolerability in comparison with conventional preparations.

In another test conducted on dogs (by the method of M. F. Makula et al., Developm. biol. Standard 67 (1987), 257-65), the tolerablity of immunoglobulin-G solutions manufactured in accordance with the invention was tested against that of conventionally manufactured preparations. This model is mainly concerned with determining the effects of polymeric materials (aggregates) by measuring changes in cardiac output. Table 5 summarizes the results.

TABLE 5

| Preparation | | % Deviation in Cardiac output | % HPSEC | Vasoactive substance[1] | | |
|---|---|---|---|---|---|---|
| | | | | Aggregates, krein | Prekallikrein | Kalkininogen |
| 8[2] | (ref.) | −50 | 1.1 | + | + | + |
| 9[3] | (ref.) | −49 | 1.91 | ++ | + | + |
| 10* | (inv.) | 0 | 0.00 | − | − | − |
| 11** | (inv.) | −13 | 0.00 | − | − | − |
| 12*** | (inv.) | 0 | 0.00 | − | − | − |

[1] Determined by Ouchterlony's immunodiffusion
[2] Raw immunoglobulin-G fraction obtained by chromatography as described in Example 5.
[3] Raw immunoglobulin-G fraction obtained by Cohn's procedure as described in Example 1.
*Manufactured as described in Example 1 of the present invention.
**Manufactured as described in Example 8 of the present invention.
***Manufactured as described in Example 5 of the present invention.

The solution is considered tolerable at cardiac output drops to −15%.

As this test also demonstrates, the preparations manufactured in accordance with the invention are higher in purity and accordingly freer of side effects than are the previously known products. The complete removal of aggregates, proteolytic substances and vasoactive compounds allows the manufacture of immunoglobulin-G preparations that can even be employed with immunosuppressed patients.

The invention will now be specified with reference to the following examples.

EXAMPLE 5 kg of Cohn's paste II are dissolved in 45 l of a buffer consisting of 0.1 m/l of sodium chloride and 0.075 m/l of sodium acetate with a pH of 5.5. The batch is treated with 10 ml of octanoic acid per liter of solution and is stirred for 1 hour at room temperature. The solution is cooled to 0° C., treated with 12.3 g of calcium acetate per liter of solution, stirred for 3 hours, and filtered. The clear filtrate is diafiltered against 10 times its volume of a 0.022-m/l Tris buffer, i.le. tris-(hydroxymethyl)-aminomethane, at a pH of 7.0 and adjusted to a protein concentration of 4%. The 4% solution is treated with 0.05% β-propiolactone at a pH of 7.2 and stirred for 12 hours at a constant pH. The solution is then diluted with a 0.022-m/l Tris buffer to a protein content of 1% and irradiated in a continuous-flow ultraviolet sterilizer at 20 l an hour.

2 g of sodium chloride per liter are added and the solution is filtered sterile.

The solution is purified by chromatography with a preparative HPLC system equipped with a 5-liter HPLC column packed with QMA-Accell.

The column is equilibrated with a buffer consisting of 0.022 m/l of Tris and 0.035 m/l of sodium chloride at a pH of 7.0 and the immunoglobulin solution chromatographed in portions of 15 l. Contaminants and aggregates attach to the chromatography phase and the high-purity immunoglobulin-G fraction passes through the column without attaching. 8 cycles are necessary to purify the whole batch. One cycle, including protein application, elution, and regeneration, takes 2 hours.

The purified immunoglobulin fraction is concentrated to 50 g/l in an ultrafiltration apparatus (cutoff at 10 000 D) and diafiltered against 10 times its volume of a 0.45% solution of sodium chloride. 0.15 m/l of glycine are added and the solution is filtered sterile.

The resulting immunoglobulin-G solution has the following properties:

| Protein (g/l) | 50.9 |
|---|---|
| Immunoglobulin G (g/l) | 52.5 |
| CAF (gamma %) | 100.0 |
| KBR (μlC/mg protein) | 6.0 |
| Proteolytic activity (U/l) | 0.3 |
| HPSEC | |
| Polymer content (%) | 0.0 |
| Prekallikrein* | neg. |
| Kallikrein* | neg. |
| Kininogen* | neg. |
| Factor XI (U/ml) | neg. |
| Prekallikrein activator (%) | neg. |

*Determined by Ouchterlony's immunodiffusion.

EXAMPLE 2

The procedure described in Example 1 is followed.

The chromatography is carried out at normal pressure in a 5-l column of WMA-Accell. 15 l of the sterilized immunoglobulin-G solution can be purified in one cycle of 4½ hours.

The remaining steps are carried out as described in Example 1.

The resulting immunoglobulin-G solution has the following properties:

| | |
|---|---|
| Protein (g/l) | 62.2 |
| Immunoglobulin G (g/l) | 61.0 |
| CAF (gamma %) | 100.0 |
| KBR (μlC/mg protein) | 13.0 |
| Proteolytic activity (U/l) HPSEC | 1.2 |
| Polymer content (%) | 0.17 |
| Prekallikrein* | neg. |
| Kallikrein* | neg. |
| Kininogen* | neg. |
| Factor XI (U/ml) | neg. |
| Prekallikrein activator (%) | neg. |

*Determined by Ouchterlony's immunodiffusion.

EXAMPLE 3

The procedure of Example 2 is followed.

DEAE-Spherosil-LS is employed for the chromatography phase instead of the 5-1 WMA-Accell column.

The resulting immunoglobulin-G solution has the following properties:

| | |
|---|---|
| Protein (g/l) | 48.0 |
| Immunoglobulin G (g/l) | 47.4 |
| CAF (gamma %) | 100.0 |
| KBR (μlC/mg protein) | 16.0 |
| Proteolytic activity (U/l) HPSEC | 0.8 |
| Polymer content (%) | 0.0 |
| Prekallikrein* | neg. |
| Kallikrein* | neg. |
| Kininogen* | neg. |
| Factor XI (U/ml) | neg. |
| Prekallikrein activator (%) | neg. |

*Determined by Ouchterlony's immunodiffusion.

EXAMPLE 4

The procedure described in Example 1 is followed.

The clear filtrate resulting from the octanoic acid treatment is diafiltered against 10 times its volume of a buffer consisting of 0.025 m/l of sodium acetate at a pH of 7.0 and adjusted to 4% protein.

The treatment with β-propiolactone and ultraviolet light described in Example 1 is carried out. To the sterilized solution 2 g of sodium chloride per liter, are added its pH is adjusted to 5.0, and it is filtered sterile.

CM-Accell is employed for the chromatography phase. The column is equilibrated with 0.025 m/l of sodium acetate and 0.035 m/l of sodium chloride at a pH of 5.0 and attaches the immunoglobulin G. It is eluted with 0.025 m/l of sodium acetate and 0.200 m/l of sodium chloride at a pH of 5.0.

The further procedure is as described in Example 1.

The resulting immunoglobulin-G solution has the following properties:

| | |
|---|---|
| Protein (g/l) | 50.00 |
| Immunoglobulin G (g/l) | 51.03 |
| CAF (gamma %) | 100.00 |
| KBR (μlC/mg protein) | 11.00 |
| Proteolytic activity (U/l) HPSEC | 0.50 |
| Polymer content (%) | 0.00 |
| Prekallikrein* | neg. |
| Kallikrein* | neg. |
| Kininogen* | neg. |
| Factor XI (U/ml) | neg. |
| Prekallikrein activator (%) | neg. |

*Determined by Ouchterlony's immunodiffusion.

EXAMPLE 5

Fresh-frozen human blood plasma is thawed at +4° C. and the cryoprecipitate centrifuged out. The PPSB-complex coagulation factors are removed by batch adaption onto Sephadex A 50. The ion exchanger is removed and the supernatant treated with 9% alcohol by volume at a pH of 5.3. The precipitate is centrifuged out. The resulting plasma, freed of coagulation factors, is adjusted by gel-exclusion chromatography (on Sephadex G-25) to an ionic environment of 0.022 m/l of Tris-HCl and a pH of 7.5.

The immunoglobulin G is separated from the other plasma proteins in a column packed with DEAE Trisacryl-LS and equilibrated with the same buffer. The raw immunoglobulin is obtained in the permeating fraction, which is concentrated to 40 g of protein per liter by ultrafiltration.

5.8 g of sodium chloride and 10.2 g of sodium acetate is added to each liter of solution, the pH is adjusted to 5.5, and the solution is treated with 10 ml of octanoic acid. The reaction is allowed to occur for 1 hour at room temperature, 12.3 g of calcium acetate per liter are added, and the solution is stirred 3 hours at 0° C.

The reaction mixture is filtered, diafiltered against 10 times its volume of a buffer consisting of 0.025 m/l of sodium acetate and 0.140 m/l of sodium chloride at a pH of 7.0, and adjusted to 4% protein.

The solution is sterilized with β-propiolactone and ultraviolet light as described in Example 1.

The pH of the sterilized immunoglobulin-G solution is adjusted to 5.0.

The chromatography is carried out in a column packed with CM-Accell and equilibrated with 0.025 m/l of sodium acetate and 0.140 m/l of sodium chloride at a pH of 5.0. 9 l of sterilized immunoglobulin-G solution are applied per liter of the chromatography phase. Subject to these conditions, the contaminants and aggregates attach to the phase and the high-purity immunoglobulin-G fraction passes through the column.

Further processing is carried out as described in Example 1.

The resulting immunoglobulin-G solution has the following properties:

| | |
|---|---|
| Protein (g/l) | 50.2 |
| Immunoglobulin G (g/l) | 51.5 |
| CAF (gamma %) | 100.0 |
| KBR (μlC/mg protein) | 5.0 |
| Proteolytic activity (U/l) HPSEC | 0.0 |
| Polymer content (%) | 0.0 |
| Prekallikrein* | neg. |
| Kallikrein* | neg. |
| Kininogen* | neg. |
| Factor XI (U/ml) | neg. |
| Prekallikrein activator (%) | neg. |

*Determined by Ouchterlony's immunodiffusion.

EXAMPLE 6

The procedure described in Example 5 is followed.

The chromatographically isolated immunoglobulin-G solution is treated with octanoic acid, sterilized, adjusted to a pH of 5.0, and filtered sterile.

The next chromatography is carried out in a column packed with SP-Trisacryl-LS and equilibrated with 0.025 m/l of sodium acetate and 0.150 m/l of sodium chloride at a pH of 5.0. 3 liters of the sterilized immunoglobulin-G solution are applied per liter of the chromatography phase.

The rest of the procedure corresponds to what is described in Example 5.

The resulting immunoglobulin-G solution has the following properties:

| | |
|---|---|
| Protein (g/l) | 49.3 |
| Immunoglobulin G (g/l) | 48.1 |
| CAF (gamma %) | 100.0 |
| KBR (μlC/mg protein) | 21.0 |
| Proteolytic activity (U/l) HPSEC | |
| Polymer content (%) | 0.0 |
| Prekallikrein* | neg. |
| Kallikrein* | neg. |
| Kininogen* | neg. |
| Factor XI (U/ml) | neg. |
| Prekallikrein activator (%) | neg. |

*Determined by Ouchterlony's immunodiffusion.

EXAMPLE 7

The procedure described in Example 5 is followed.

The chromatographically isolated immunoglobulin-G solution is treated with octanoic acid, diafiltered against 10 times its volume of a 0.1-m/l phosphate buffer at a pH of 7.0, and adjusted to 4% protein.

The solution is sterilized with β-propiolactone and ultraviolet light as described in Example 1.

The sterilized immunoglobulin-G solution with a protein content of 1% is treated with solid ammonium sulfate to a final concentration of 1 mole of ammonium sulfate per liter and filtered sterile.

An HPLC column packed with Polypropyl-A is equilibrated with a buffer consisting of 1 m/l of ammonium sulfate and 0.1 m/l of phosphate at a pH of 7.0. 2 liters of the adjusted immunoglobulin-G solutions are applied per liter of the chromatography phase. Subject to these conditions the immunoglobulin G attaches to the phase and the contaminants are rinsed out with the equilibration buffer. The immunoglobulin-G fraction is eluted with 0.1 m/l of phosphate at a pH of 7.0.

The rest of the procedure is as described in Example 1.

The resulting immunoglobulin-G solution has the following properties:

| | |
|---|---|
| Protein (g/l) | 51.0 |
| Immunoglobulin G (g/l) | 56.3 |
| CAF (gamma %) | 99.3 |
| KBR (μlC/mg protein) | 12.0 |
| Proteolytic activity (U/l) HPSEC | 0.50 |
| Polymer content (%) | 0.1 |
| Prekallikrein* | neg. |
| Kallikrein* | neg. |
| Kininogen* | neg. |
| Factor XI (U/ml) | 0.01 |
| Prekallikrein activator (%) | neg. |

*Determined by Ouchterlony's immunodiffusion.

EXAMPLE 8

The procedure described in Example 5 is followed.

The immunoglobulin-G fraction is concentrated to 40 g/l and treated with 8.2 g of sodium chloride and 2.05 g of sodium acetate per liter of solution are added and subjected as described in Example 1 to sterilization with β-propiolactone and ultraviolet light.

The pH of the sterilized immunoglobulin-G is adjusted to 5.0.

The solution is chromatographed in a column packed with CM-Accell and equilibrated with 0.025 m/l of sodium acetate and 0.140 m/l of sodium chloride at a pH of 5.0.

The high-purity immunoglobulin-G fraction passes through the column and the contaminants and aggregates attach to the phase.

Further processing is as described in Example 1.

The resulting immunoglobulin-G solution has the following properties:

| | |
|---|---|
| Protein (g/l) | 101.1 |
| Immunoglobulin G (g/l) | 102.0 |
| CAF (gamma %) | 100.0 |
| KBR (μlC/mg protein) | 7.0 |
| Proteolytic activity (U/l) HPSEC | 1.2 |
| Polymer content (%) | 0.0 |
| Prekallikrein* | neg. |
| Kallikrein* | neg. |
| Kininogen* | neg. |
| Factor XI (U/ml) | neg. |
| Prekallikrein activator (%) | neg. |

*Determined by Ouchterlony's immunodiffusion.

EXAMPLE 9

The procedure of Example 5 is followed.

To the chromatographically isolated and sterilized immunoglobulin-G solution 9 g of sodium chloride and 2.05 g of sodium acetate per liter of solution and the pH is adjusted to 5.0.

The chromatography is carried out in a column packed with SP-Trisacryl-LS and equilibrated with 0.025 mole of sodium acetate and 0.150 m/l of sodium chloride at a pH of 5.0.

The procedure continues as described in Example 5.

The resulting immunoglobulin-G solution has the following properties:

| | |
|---|---|
| protein (g/l) | 98.5 |
| Immunoglobulin G (g/l) | 96.2 |
| CAF (gamma %) | 100.0 |
| KBR (μlC/mg protein) | 19.0 |
| Proteolytic activity (U/l) HPSEC | 0.8 |
| Polymer content (%) | 0.0 |
| Prekallikrein* | neg. |
| Kallikrein* | neg. |
| Kininogen* | neg. |
| Factor XI (U/ml) | neg. |
| Prekallikrein activator (%) | neg. |

*Determined by Ouchterlony's immunodiffusion.

| Cation exchangers | |
|---|---|
| CM-Accell: | polyvinyl coated silica substituted with carboxymethyl groups. |
| SP-Trisacryl-LS: | copolymers of N-arylolyl-2-amino-2-hydroxymethyl-1,3-propanediol |

|  |  |
|---|---|
|  | and a hydroxylated acrylic bifunctional monomer substituted with sulfopropyl or carboxymethyl groups. |
| SP-Spherodex: | dextran coated silica substituted with sulfopropyl groups. |
| Franktogel-TSK-SP 650: | copolymer from oligoethylenglycole, glycidylmethacrylate and pentaerthrolidimethacrylate substituted with sulfopropyl groups. |
| Anion exchangers: | |
| DEAE-Spherosil: | polymer coated silica substituted with diethyl-aminomethyl groups. |
| QMA-Accell: | polyvinyl coated silica substituted with quaternary aminoethyl groups. |
| Hydrophobic interaction material: | |
| Polyol A: | Silica coated with polyaspartamide and 3-aminopropyltrihydroxysilane. |

It will be appreciated that the instant specification and claims are set forth by way of illustration and not limitation, and that various modifications and changes may be made without departing from the spirit and scope of the present invention.

We claim:

1. A method for removing proteolytic enzymes, vasoactive substances and aggregates with no significant precipitation of proteins from a composition of matter containing immunoglobulin-G, proteolytic enzymes, vasoactive substances, and aggregates and from which fibrinogen, factor VIII, factor IX, factor VII, factor II, and factor X have been removed, said method comprising:
   (a) contacting the composition of matter with 0.4 to 1.5% by volume of octanoic acid to yield a solution of the composition of matter and the octanoic acid and then purifying the solution by chromatography.

2. The method according to claim 1, wherein the contacting in step (a) is with 0.8 to 1% of octanoic acid by volume.

3. The method according to claim 1, wherein the chromatography is carried out on a phase appropriate for high-performance liquid chromatography (HPLC).

4. The method according to claim 1, wherein the chromatography is effected on QMA-Accell or DEAE-Spherosil as an anion exchanger.

5. The method according to claim 1, wherein the chromatography is effected on CM-Accell, SP-Spherodex, SP-Trisacryl-LS, or Fraktogel TSK SP 650 as a cation exchanger.

6. The method according to claims 1, wherein the chromatography is carried out on a hydrophobic phase in the form of Polypropyl A.

7. The method according to claim 1, wherein the chromatography is carried out on an anion exchanger at an ion concentration of 0 to 50 mmoles/l of sodium chloride and a pH of 6.0 to 8.0.

8. The method according to claim 1, wherein the chromatography is carried out on a cation exchanger at an ion concentration of 50 to 200 mmoles/l of sodium chloride and a pH of 4.0 to 6.0.

9. The method according to claim 1, wherein prior to the purification of step (a) sterilization is effected with $\beta$-propiolactone, TNBP+Tween, TNBP and sodium cholate, or TNBP.

10. The method according to claim 9, wherein the sterilization also includes exposure to ultraviolet light.

11. The method according to claim 10, wherein the sterilization is carried out with 0.03 to 0.1% by volume of $\beta$-propiolactone and ultraviolet light.

12. The method according to claim 1, wherein the composition of matter is a gamma-globulin fraction (Cohn's paste II or II-III) obtained by Cohn's fractionation.

13. The method according to claim 1, wherein the composition of matter is an immunoglobulin-G fraction obtained from plasma with a precipitant comprising polyethylene glycol or ammonium sulfate.

14. The method according to claim 1, wherein the composition of matter is a raw solution that contains immunoglobulin G and was previously chromatographically purified from serum.

15. The method according to claim 1, wherein the composition of matter is a fraction that contains immunoglobulin G and has high antibody titers against viral, bacterial or cellular antigens.

* * * * *